United States Patent
Otvos

(10) Patent No.: US 8,492,515 B2
(45) Date of Patent: Jul. 23, 2013

(54) ANTIBACTERIAL PEPTIDES ACTIVE IN SYSTEMIC INFECTIONS

(75) Inventor: Laszlo Otvos, Audubon, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 313 days.

(21) Appl. No.: 12/866,864

(22) PCT Filed: Feb. 27, 2009

(86) PCT No.: PCT/US2009/001241
§ 371 (c)(1),
(2), (4) Date: Aug. 9, 2010

(87) PCT Pub. No.: WO2009/108347
PCT Pub. Date: Sep. 3, 2009

(65) Prior Publication Data
US 2010/0323951 A1    Dec. 23, 2010

Related U.S. Application Data

(60) Provisional application No. 61/067,509, filed on Feb. 28, 2008.

(51) Int. Cl.
*A61K 38/00* (2006.01)
(52) U.S. Cl.
USPC .......................... 530/326; 514/2.4; 514/21.4
(58) Field of Classification Search
None
See application file for complete search history.

(56) References Cited

U.S. PATENT DOCUMENTS

2006/0287238 A1    12/2006    Sturgess et al. ................. 514/13

OTHER PUBLICATIONS

Otvos, Laszlo et. al. Designer Antibacterial Peptides Kill Flouroquinolone-Resistant Clinical isolates, J. Med. Chem. (48) 5349-5359, 2005.*
Bergland et. al. A Proline-Rich Chitinase from *Beta vulgaris*, Plant Molecular Biology 27:211-216, 1995.*
Cassone, M., et al. "Scope and limitation of the designer proline-rich antibacterial peptide dimmer, A3-APO, alone or in synergy with conventional antibiotics," *Peptides*, 29, pp. 1878-1886 (2008).
Noto, P.B., et al. "Alternative stabilities of a proline-rich antibacterial peptide in vitro and in vivo," *Protein Science*, 17, pp. 1249-1255 (2008).
Otvos Jr., L., et al. "Designer antibacterial peptides kill fluoroquinolone-resistant clinical isolates," J. Med. Chem., 48, pp. 5349-5359 (2005).

* cited by examiner

*Primary Examiner* — Christina Bradley
*Assistant Examiner* — Jeanette Lieb
(74) *Attorney, Agent, or Firm* — Drinker Biddle & Reath LLP

(57) ABSTRACT

Antimicrobial peptides of the formula are provided: $X_1$—$X_2$—PrO—$X_3$—$X_4$—PrO-Arg-Pro-Tyr-Leu-Pro-$X_5$-Pro-Arg-Pro-Pro-Arg-Pro-Y, wherein $X_1$ is a natural or non-natural amino acid having a free amino group or 1-aminocyclohexyl carboxylic acid, $X_2$ is Arg or N-methyl-Arg, $X_3$ is Asp or Glu, $X_4$ is Arg or Lys, $X_5$ is Arg or Lys, and Y is Arg, Arg-NH2, N-methyl-Arg, N-methyl-Arg-$NH_2$, Val-Arg, Val-Arg-$NH_2$, Val-(N-methyl-Arg), or Val-(N-methyl)-Arg-$NH_2$, and salts thereof.

13 Claims, 5 Drawing Sheets

SEQUENCE LISTING

<160> NUMBER OF SEQ ID NOS: 7

<210> SEQ ID NO 1
<211> LENGTH: 20
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: 1-amino-cyclohexyl carboxylic acid

<400> SEQUENCE: 1

Xaa Arg Pro Asp Lys Pro Arg Pro Tyr Leu Pro Arg Pro Arg Pro Pro
1               5                   10                  15

Arg Pro Val Arg
            20

<210> SEQ ID NO 2
<211> LENGTH: 19
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: 1-amino-cyclohexyl carboxylic acid

<400> SEQUENCE: 2

Xaa Arg Pro Asp Lys Pro Arg Pro Tyr Leu Pro Arg Pro Arg Pro Pro
1               5                   10                  15

Arg Pro Val

<210> SEQ ID NO 3
<211> LENGTH: 20
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: 1-amino-cyclohexyl carboxylic acid
<220> FEATURE:
<221> NAME/KEY: MOD_RES
<222> LOCATION: (20)..(20)
<223> OTHER INFORMATION: amidation

<400> SEQUENCE: 3

Xaa Arg Pro Asp Lys Pro Arg Pro Tyr Leu Pro Arg Pro Arg Pro Pro
1               5                   10                  15

Arg Pro Val Arg
            20

<210> SEQ ID NO 4
<211> LENGTH: 14
<212> TYPE: PRT
<213> ORGANISM: Artificial Sequence
<220> FEATURE:
<223> OTHER INFORMATION: Chemically artificially synthesized

<400> SEQUENCE: 4

Arg Pro Tyr Leu Pro Arg Pro Arg Pro Pro Arg Pro Val Arg
1               5                   10

```
<210> SEQ ID NO 5
<211> LENGTH: 18
<212> TYPE: PRT
<213> ORGANISM: Artificial Sequence
<220> FEATURE:
<223> OTHER INFORMATION: Chemically artificially synthesized

<400> SEQUENCE: 5

Asp Lys Gly Ser Tyr Leu Pro Arg Pro Thr Pro Pro Arg Pro Ile Tyr
1               5                   10                  15

Asn Arg

<210> SEQ ID NO 6
<211> LENGTH: 20
<212> TYPE: PRT
<213> ORGANISM: Artificial Sequence
<220> FEATURE:
<223> OTHER INFORMATION: Chemically artificially synthesized
<220> FEATURE:
<221> NAME/KEY: VARIANT
<222> LOCATION: (1)..(1)
<223> OTHER INFORMATION: is a natural or non-natural amino acid having a
      free amino group, or 1-amino-cyclohexyl carboxylic acid.
<220> FEATURE:
<221> NAME/KEY: VARIANT
<222> LOCATION: (2)..(2)
<223> OTHER INFORMATION: is Arg or N-methyl-Arg
<220> FEATURE:
<221> NAME/KEY: VARIANT
<222> LOCATION: (4)..(4)
<223> OTHER INFORMATION: is Asp or Glu
<220> FEATURE:
<221> NAME/KEY: VARIANT
<222> LOCATION: (5)..(5)
<223> OTHER INFORMATION: is Arg or Lys
<220> FEATURE:
<221> NAME/KEY: VARIANT
<222> LOCATION: (12)..(12)
<223> OTHER INFORMATION: is Arg or Lys
<220> FEATURE:
<221> NAME/KEY: VARIANT
<222> LOCATION: (19)..(19)
<223> OTHER INFORMATION: is Arg, Arg-NH2, N-methyl-Arg, N-methyl-Arg-NH2
      or Val
<220> FEATURE:
<221> NAME/KEY: VARIANT
<222> LOCATION: (20)..(20)
<223> OTHER INFORMATION: is Arg, Arg-NH2, N-methyl-Arg or
      N-methyl-Arg-NH2 when position 19 is Val; otherwise, when position
      19 is other than Val, no amino acid

<400> SEQUENCE: 6

Xaa Xaa Pro Xaa Xaa Pro Arg Pro Tyr Leu Pro Xaa Pro Arg Pro Pro
1               5                   10                  15

Arg Pro Xaa Xaa
            20

<210> SEQ ID NO 7
<211> LENGTH: 21
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: 1-amino-cyclohexyl carboxylic acid
<220> FEATURE:
<221> NAME/KEY: MOD_RES
<222> LOCATION: (21)..(21)
<223> OTHER INFORMATION: 2,4-diamino butyric acid

<400> SEQUENCE: 7
```

```
Xaa Arg Pro Asp Lys Pro Arg Pro Tyr Leu Pro Arg Pro Arg Pro Pro
1               5                   10                  15

Arg Pro Val Arg Xaa
            20
```

ANTIBACTERIAL PEPTIDES ACTIVE IN SYSTEMIC INFECTIONS

This application claims the benefit from U.S. Provisional Application No. 61/067,509, filed Feb. 28, 2008, the entire disclosure of which is incorporated herein by reference in its entirety.

FIELD OF THE INVENTION

The invention relates to antimicrobial peptides for treatment of bacterial infections.

BACKGROUND OF THE INVENTION

Antimicrobial peptides have historically been a primary focus of peptide research (Hancock, R. E., and Scott, M. G. 2000. *Proc. Natl. Acad. Sci. USA* 97: 8856-8861). Their size makes them amenable to detailed structure-activity studies, and the measurement of their cellular efficacy is relatively simple, even if assay conditions have to be adjusted to fit peptide antibiotics (Cudic et al., 2002. *Peptides* 23: 271-283). Naturally, the most active derivates were considered viable alternatives to small molecules in antimicrobial drug therapy (Zasloff, M. 2002. *Nature* 415: 389-395).

Resistance induction is rarely seen with peptide-based antimicrobials compared to traditional antibiotics (Ge, et al., 1999. *Antimicrob. Agents Chemother.* 43: 782-788), but their parenteral use is occasionally hampered by inadequate safety margins and frequently by rapid clearance, leaving them suitable only for topical applications (Bush et al., 2004. *Curr. Opin. Microbiol.* 7: 466-476). A designer proline-rich peptide dimer was recently described, A3-APO, that kills bacteria by a dual mode of action, and thus is able to kill multidrug resistant clinical isolates of Enterobactericeae in vitro, in concentrations acceptable for clinical development (Otvos et al., 2005. *J. Med. Chem.* 48: 5349-5359). A3-APO, one of the most potent peptide antibiotics to date, appears to combine the positive features of non-toxic membrane-active antibacterial peptides (Chen et al., 2005. *J. Biol. Chem.* 280: 12316-12329) and those acting on intracellular targets (Cudic and Otvos, 2002. *Curr. Drug Targets* 3: 101-106). The bacterial target of A3-APO, similar to many other native proline-rich antimicrobial peptides, is the C-terminal D-E helix of the 70 kDa bacterial heat shock protein DnaK (Otvos et al., 2005. *J. Med. Chem.* 48: 5349-5359; Kragol et al., 2001. *Biochemistry* 40: 3016-3026; Bikker et al., 2006. *Chem. Biol. Drug Des.* 68: 148-153).

Typically, the first steps for progressing from in vitro efficacy measurements to in vivo evaluation of activity and ensuing clinical development are the assessments of peptide stability in vitro and pharmacokinetics in vivo. Serum stability is considered the most important secondary screening assay in drug discovery because it can identify peptides that are unstable in body fluids and thus will fail in the development process (Powell et al., 1993. *Pharm. Res.* 10: 1268-1273). Pharmacokinetics can identify a 1-hour time period needed for full bacterial killing of the proline-rich peptides with intracellular targets (Cudic et al., 1999. *Eur. J. Biochem.* 266: 559-565), when the peptide concentration in serum exceeds 130% of the in vitro minimal inhibitory concentration (MIC) value, a minimal dose required for in vivo efficacy (Bush et al., 2004. *Curr. Opin. Microbiol.* 7: 466-476).

The extent of the decomposition of peptide A3-APO gradually increases from in vitro to ex vivo and in vivo in murine models. This necessarily results in a significantly larger dose of A3-APO required for in vivo efficacy studies than it would be calculated from the in vitro stability data. Therefore, a need exists for a stable peptide that effectively kills bacteria and protects mammals from lethal or sublethal infections in vivo, without exhibiting immunogenic properties.

SUMMARY OF THE INVENTION

Compounds of the invention are useful as antimicrobial peptides for treatment of bacterial infections.

According to the invention, an isolated and purified compound is provided according to formula I:

(I)

(SEQ ID NO: 6)
$X_1$-$X_2$-Pro-$X_3$-$X_4$-Pro-Arg-Pro-Tyr-Leu-Pro-$X_5$-Pro-

Arg-Pro-Pro-Arg-Pro-Y wherein:
(a) $X_1$ is selected from the group consisting of:
 (i) a natural or non-natural amino acid having a free amino group, and
 (ii) 1-amino-cyclohexyl carboxylic acid,
(b) $X_2$ is Arg or N-methyl-Arg,
(c) $X_3$ is Asp or Glu,
(d) $X_4$ is Arg or Lys,
(e) $X_5$ is Arg or Lys, and
(f) Y is Arg, Arg-$NH_2$, N-methyl-Arg, N-methyl-Arg-$NH_2$, Val-Arg, Val-Arg-$NH_2$, Val-(N-methyl-Arg), or Val-(N-methyl)-Arg-$NH_2$.

An aspect of the invention also includes a salt of any of the compounds of formula I.

According to one embodiment, a compound of formula I has the amino acid sequence:

(SEQ ID NO: 2)
Chex-Arg-Pro-Asp-Lys-Pro-Arg-Pro-Tyr-Leu-Pro-Arg-

Pro-Arg--Pro-Pro-Arg-Pro-Val-Arg or:

(SEQ ID NO: 3)
Chex-Arg-Pro-Asp-Lys-Pro-Arg-Pro-Tyr-Leu-Pro-Arg-

Pro-Arg--Pro-Pro-Arg-Pro-Val-Arg-$NH_2$ or salts thereof.

The peptide of SEQ ID NO:2 may also be referred to herein as "Chex1-Arg20". The peptide of SEQ ID NO:3 may be referred to herein as "Chex1-Arg20-$NH_2$".

The invention includes a pharmaceutical composition comprising a compound of formula I, or a salt thereof, and a pharmaceutically-acceptable carrier. The invention also includes a pharmaceutical composition comprising a compound of formula I, or a salt thereof, a non-peptide antibiotic, and a pharmaceutically-acceptable carrier.

The invention includes a method of treating a bacterial infection in a subject in need of such treatment, the method comprising administering to the subject an effective amount of an isolated and purified compound of formula I, or a salt thereof, or a pharmaceutical composition, as above. The invention also includes a method of treating a bacterial infection in a subject in need of such treatment, the method comprising administering to the subject an effective amount of an isolated and purified compound of formula I, or a salt thereof, and a non-peptide antibiotic. In one embodiment of the of the aforesaid methods and compositions, the compound of formula I is the compound of SEQ ID NO:2 or SEQ ID NO:3, or salts thereof.

BRIEF DESCRIPTION OF THE DRAWINGS

Embodiments of the present invention will now be described, by way of example only, with reference to the attached Figures.

In FIG. 4A the symbols represent bacterial counts observed for infected and non-treated mice, A3-APO treated mice and imipenem treated mice. In FIG. 4B the symbols represent bacterial counts observed for infected and non-treated mice, Chex1-Arg20-NH$_2$ treated mice and imipenem treated mice. Identical shapes if FIGS. 4A and 4B represent identical timepoints, respectively.

ABBREVIATIONS AND SHORT FORMS

Figure 1:
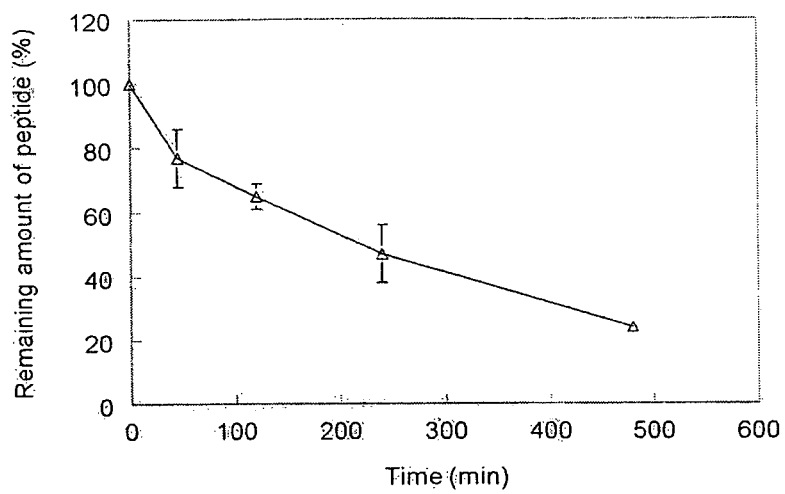
FIG. 1 illustrates the degradation of peptide A3-APO in 25% pooled mouse serum. The peptide was incubated with the serum for different time periods and the remaining peptide amounts were determined by reversed-phase high performance liquid chromatography.

The following abbreviations and short forms are used in this specification.

"Chex" is 1-amino-cyclohexane-carboxylic acid.
"Dab" is 2,4-diamino-butyric acid.
"MS" means mass spectroscopy.

DETAILED DESCRIPTION

I. Definitions

As used in the specification and the appended claims, the singular forms "a," "an" and "the" include plural referents unless the context clearly dictates otherwise.

The expressions "treat" and "treatment" mean cause, or the act of causing, a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

The expression "effective amount", when used to describe therapy to an individual, refers to the amount of a compound that results in a therapeutically useful effect.

As used herein, "individual" (as in the subject of the treatment) means mammals, particularly non-human primates, e.g. apes and monkeys, and most particularly humans.

Peptides are defined herein as organic compounds comprising a chain of two or more amino acids covalently joined by peptide bonds. Peptides may be referred to with respect to the number of constituent amino acids, i.e., a dipeptide contains two amino acid residues, a tripeptide contains three, etc. A "peptide" as used in the presently claimed invention is intended to refer to a moiety with a molecular weight of less than 10,000 Daltons.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "isolated and purified" means a compound substantially free of contaminants or cell components with which the compound may naturally occur, or the reagents used in synthesis or the byproducts of synthesis. "Isolated" and "substantially free of contaminants" does not mean that the preparation is technically pure (homogeneous), but it is sufficiently pure to provide the peptide or polypeptide in a form in which it can be used therapeutically.

The term "antibacterial activity" means any activity that destroys bacteria or suppresses bacterial growth or the ability of bacteria to reproduce.

The term "acetylated amino acid" means an amino acid having an acetyl moiety in its side chain.

An amino acid derivative indicated as comprising a linked amino group, such as "Arg-NH$_2$", for example, refers to an amino amide derivative wherein the carboxylic acid function of the amino acid is converted to an amide, i.e., NH$_2$—CH(R)—C(O)—NH$_2$ wherein R is the amino acid side chain.

II. Compounds of the Invention

In one aspect of the invention, there is provided an isolated and purified compound of the formula I, or salt thereof:

(I)
(SEQ ID NO: 6)
X$_1$-X$_2$-Pro-X$_3$-X$_4$-Pro-Arg-Pro-Tyr-Leu-Pro-X$_5$-Pro-Arg-Pro-Pro-Arg-Pro-Y wherein:
(a) X$_1$ is selected from the group consisting of:
  (i) a natural or non-natural amino acid having a free amino group, and
  (ii) 1-amino-cyclohexyl carboxylic acid,
(b) X$_2$ is Arg or N-methyl-Arg,
(c) X$_3$ is Asp or Glu,
(d) X$_4$ is Arg or Lys,
(e) X$_5$ is Arg or Lys, and
(f) Y is Arg, Ara-NH$_2$, N-methyl-Arg, N-methyl-Arg-NH$_2$, Val-Arg, Val-Arg-NH$_2$, Val-(N-methyl-Arg), or Val-(N-methyl)-Arg-NH$_2$.

a. Preparation of Compounds of the Invention

The compounds of the invention may be prepared by methods known to the person skilled in the art of peptide and organic synthesis.

Peptides of the present invention may be natural peptides, recombinant peptides or synthetic peptides. They may also be chemically synthesized, using, for example, solid phase synthesis methods. In a preferred method, the synthesis and analysis of peptides are described in (Otvos et al., 2005. *J. Med. Chem.* 48: 5349-5359, Cudic et al., 2002. *Peptides* 23: 271-283)

The peptides of the invention, such as the Chex1-Arg20 peptide (SEQ ID NO:2), may be made on a standard automated synthesizer. The peptides are detached from the resin and may be purified by reverse phase high pressure liquid chromatography. Matrix-assisted laser desorption/ionization (MALDI)-MS may be used to verify the accuracy of the sequences and their purity.

Alternatively, peptides may be prepared utilizing recombinant DNA technology, which comprises combining a nucleic acid encoding peptides of formula I in a suitable vector, inserting the resulting vector into a suitable host cell, recovering the peptide subsequently produced by the host cell, and purifying the polypeptide recovered. The required techniques of recombinant DNA and protein technology are known to the ordinary skilled artisan. General methods for the cloning and expression of recombinant molecules are described in *Molecular Cloning* by Sambrook et al. (Cold Spring Harbor Laboratories, Second Ed., 1989) and in *Current Protocols in Molecular Biology* by Ausubel (Wiley and Sons, 1987).

The nucleic acid encoding a desired peptide may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate in which they are administered. Selection of the appropriate regulatory region or regions is a routine matter, within the level of ordinary skill in the art.

Promoters that may be used in the synthesis of compounds of the present invention include both constitutive promoters and inducible promoters. The promoters may be prokaryotic or eukaryotic, depending on the host.

The compounds of the invention, whether prepared by chemical synthesis or recombinant DNA technology, may be purified using known techniques, for example preparative HPLC, FPLC, affinity chromatography, as well as other chromatographic methods. Isolated compounds may then be assessed for biological activity according to the methods described herein, as well as by any methods known to the skilled artisan.

For synthetic techniques, peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent.

b. Salts of Compounds of the Invention

Peptide chains typically contain acidic or basic groups (such as amine or carboxyl groups) such groups will not necessarily be in the free base form. When referring to compounds that are peptides or compounds that contain peptide chains, the reference is intended to include salt forms of the peptide. Within the scope of the invention, therefore, are salts of compounds of formula I. The preferred salts are pharmaceutically acceptable salts.

The term "salts" embraces addition salts of free acids or free bases which are compounds of the invention. The term "pharmaceutically acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aralkyl, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound according to formula I by reacting, for example, the appropriate acid or base with the compound according to formula I.

c. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

The compositions are preferably formulated in a unit dosage form, each dosage containing from about 1 to about 2 g, or alternatively from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. In an embodiment of the invention, a controlled release composition of the invention provides continuous release of an active agent over a fourteen day period of time.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The compounds of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 µg to 1 g, or alternatively from 1 µg to 20 mg of the compound of the invention per actuation and the actuation volume may vary from 1 µL to 100 µL. A typical formulation may comprise the compound of the invention, propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formula (I), a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted and programmed release. Sustained or controlled release can be obtained by using for example poly(D,L-lactic-co-glycolic acid).

III. Activity of the Compounds of the Invention

In an aspect of the present invention, a compound of the invention has antibacterial activity. As used herein, antibacterial activity means that a compound of the invention demonstrates destruction of the bacteria, and/or the suppression of bacterial growth or reproduction.

Antibacterial activity may be assayed using bacterial growth inhibition studies for the peptide or compound's ability to kill bacteria, such as Enterobacteriaceae strains, for example, in partially diluted or undiluted Muller-Hinton broth according to known methods. Antibacterial activity may also be assayed by determining the peptide or compound's ability to kill bacteria, such as Enterobacteriaceae strains, for example, in the bloodstream by measuring bacterial levels in the blood.

IV. Methods of Treatment Using Compounds of the Invention

The compounds of the invention are antibacterial peptides. These compounds have narrow-spectrum antibacterial activity. In one embodiment, the compounds of the invention are used to treat a bacteria of the family Enterobacteriaceae, such as *Escherichia coli, Klebsiella pneumoniae, Salmonella typhimurium* or *Haemophilus influenzae*, for example. The compounds of the invention may also be used to treat other bacteria, such as *Staphylococcus saprophyticus, Acinetobacter baumannii*, and *Enterobacter cloacae* for example. Thus, the compounds of the invention can be used for the treatment of bacterial infections.

In an embodiment, the invention includes a method of treating a bacterial infection in a patient identified as being in need of such treatment. The method comprises administering an effective amount of the compound, or a pharmaceutical composition comprising the compound, as described herein, to an individual in need to such treatment. An individual having a bacterial infection in the bloodstream, for example, can benefit from intravenous treatment with a compound, as described herein, because the compound has antibacterial properties against the blood-borne bacteria.

In an embodiment, the invention includes a method of prophylactic treatment of mammals, food products or other consumer products.

In another embodiment, one or more compounds of the invention may be administered to a patient in combination with one or more non-peptide antibiotics. Non-peptide antibiotics include traditional classes of antibiotics such as, but not limited to, beta-lactam antibiotics, penicillins, cephalosporins, fluoroquinolones, tetracyclines, sulfonamides, aminoglycosides, carbapenems and macrolides.

The amount of the therapeutic compound of the invention that will be effective in the treatment of a particular disorder or condition will depend on the nature of the disorder or condition, and is determined by standard clinical techniques. The precise dose to be employed in the formulation also will depend on the route of administration and the seriousness of the disease, disorder, or condition and is decided according to the judgment of the practitioner and each patient's circumstances.

In one aspect, the present invention provides peptide therapeutics for the treatment of systemic infections (i.e., bacteremia). In another aspect, the present invention provides peptide therapeutics for the treatment of local infections, such as urinary tract, gastrointestinal tract and respiratory tract infections.

V. Administration of Compounds of the Invention

The compounds of the invention may be administered by any route, including oral, rectal, pulmonary, sublingual, and parenteral administration. Parenteral administration includes, for example, intraperitoneal, intravenous, intramuscular, intraarterial, intravesical (e.g., to the bladder), intradermal, transdermal, topical or subcutaneous administration.

Typically it is contemplated that treatment would be given at least once per day, typically once, twice, three times or four times per day with the doses given at equal intervals throughout the day and night in order to maintain a constant presence of the drug in order to provide sufficient antibacterial activity. However, the skilled artisan will be aware that a treatment schedule can be optimized for any given patient, and that administration of compound may occur less frequently than once per day.

One or more compounds of the invention may be administered simultaneously, by the same or different routes, or at different times during treatment. The compounds of the invention may also be prescribed to be taken in combination with other drugs used to treat other diseases or disorders. When used in such combinations compounds of the invention and conventional drugs may be administered simultaneously, by the same or different routes, or at different times during treatment. The dose of the conventional drug selected will depend on the particular compound being used and the route and frequency of administration.

The treatment may be carried out for as long a period as necessary, i.e., until the infection is cleared or no longer a threat to the host. Typically it is contemplated that treatment would be continued indefinitely while the disease state persists, although discontinuation might be indicated if the compounds no longer produce a beneficial effect. The treating physician will know how to increase, decrease, or interrupt treatment based on patient response.

The specific dose of a compound according to the invention to obtain therapeutic benefit for treatment of an infection will, of course, be determined by the particular circumstances of the individual patient including the size, weight, age and sex of the patient, the nature and stage of the disease, the aggressiveness of the disease, and the route of administration of the compound.

For example, a daily dosage from about 0.02 to about 50 mg/kg/day may be utilized, more preferably from about 0.1 to about 20 mg/kg/day, more preferably from about 1 to about 20 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Stability of Peptide A3-APO in Dilute Serum

The stability of peptide A3-APO was analyzed in commercially available pooled mouse serum diluted to 25% with distilled water as follows. It has been shown that dilution of serum linearly reduces the degradation rate of peptides without changing any other proteolytic parameters (Powell et al., 1992. *J. Pharm. Sci.* 81: 731-735). The reduced degradation rate makes the collection and workup of the parallels more manageable for ensuing reversed-phase chromatographic analysis of peptide content. Specifically, ninety μL of pooled sterile mouse serum (Equitech-Bio, Kerrville, Tex.) was added to 10 μL of peptide A3-APO dissolved in distilled water at 1.28 mg/mL concentration. After incubation periods of 0, 15, 30, 60 or 90, 120 and 240 min at 37° C., 20 μL 15% trichloracetic acid (TCA) was added, the mixture stored at 4° C. for 20 minutes, and centrifuged at 13,000 rpm. The supernatant was submitted to determination of remaining amount of unmodified A3-APO peptide by MS and RP-HPLC.

FIG. 1 illustrates the degradation of peptide A3-APO in 25% pooled mouse serum. As shown in FIG. 1, peptide A3-APO was remarkably stable in diluted mouse serum, exhibiting a half-life of approximately 230 minutes. Calculating back to undiluted serum, this indicated that within the first hour, almost half of the original peptide amount remained intact. With a safe margin of 16 μg/mL MIC value, 1.8 mL total mouse blood volume and 20 g mouse weight, the therapeutic dose may be no more than 100 μg/mouse or 5 mg/kg. Accordingly, all ensuing stability, pharmacokinetics and immunization studies were done at 6 μg/100 μL in vitro or ex vivo or 5 mg/kg in vivo peptide doses.

Stability of Peptide A3-APO in Undiluted Serum

The metabolic stability of peptide A3-APO in full serum in vitro was examined in peptide degradation studies in blood derived media. A3-APO was added to undiluted mouse serum preparation and was incubated in the full serum for 30 minutes. The serum proteins were precipitated and the serum was submitted for mass spectroscopic analysis.

Figure 2:
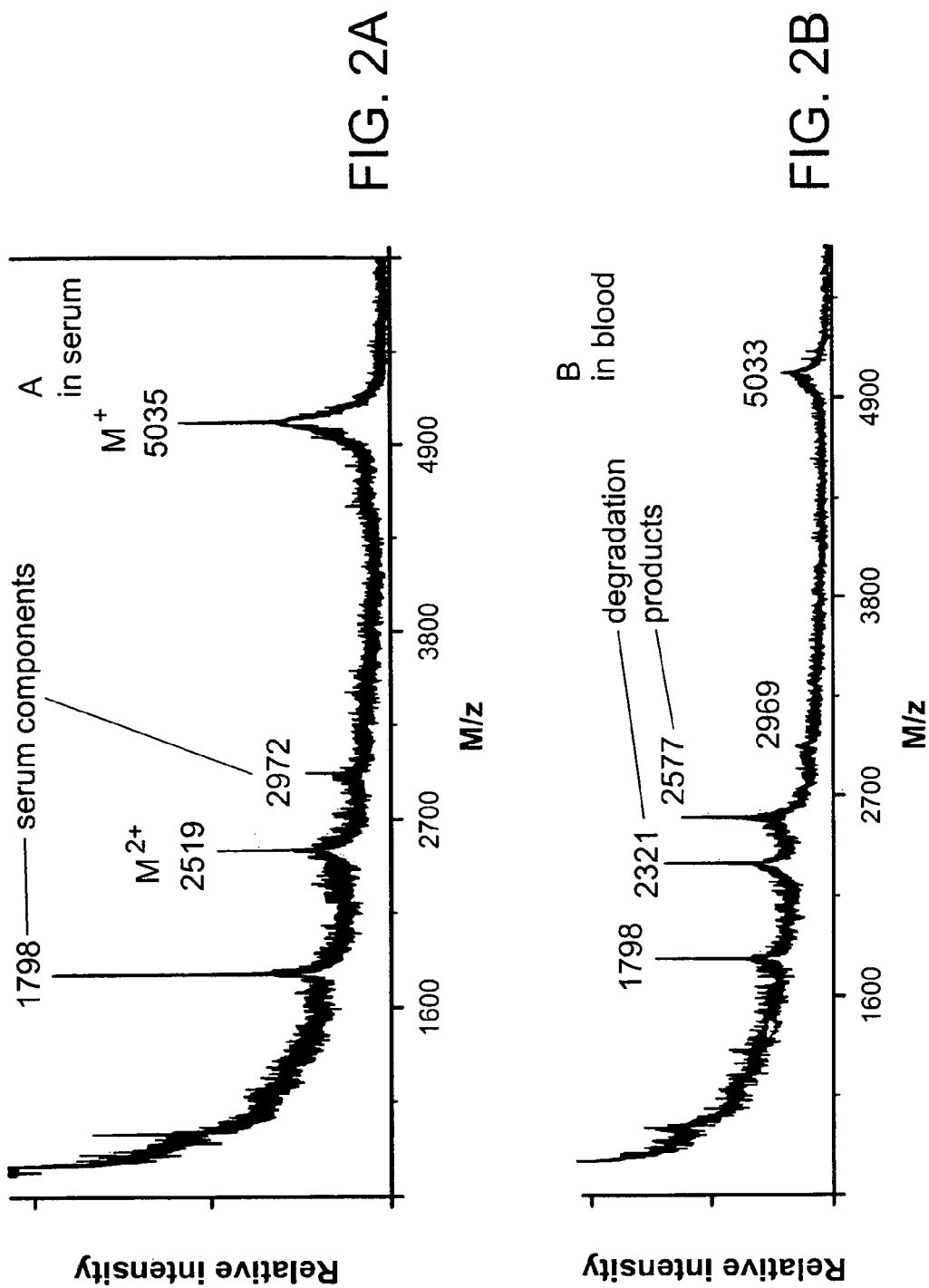
FIG. 2 illustrates the stability of peptide A3-APO in blood preparations. The peptide was incubated with commercially available 100% pooled mouse serum (upper panel) or full blood retrieved from CD-1 mice locally (lower panel) for 30 minutes. After removing the cells (in lower panel) and plasma proteins (both panels), the blood preparations were submitted to matrix-assisted laser desorption/ionization flight-of-time mass spectroscopy analysis.

As shown in the upper panel of FIG. 2, the only peptide-related peaks that could be identified corresponded to the unmodified peptide A3-APO at 5035 M/z, the double charged species at 2519 M/z and two serum components at 1798 and 2972 M/z. These peaks typically present themselves in murine blood products regardless whether test peptides are added or not. The source of these MS peaks was not identified.

According to the kinetic analysis as presented in FIG. 1, approximately 35% of peptide A3-APO had to be degraded after the 30-minute examination period. It is presumed that none of the early degradation products were stable enough to be detected by mass spectroscopy. Based on this analysis, it appears that peptide A3-APO is unusually stable in mouse serum.

Stability of Peptide A3-APO in Whole Blood

Female CD-1 mice of 8 weeks were retroorbitally bled and 6 μg A3-APO peptide dissolved in 10 μL phosphate buffered saline (PBS) was immediately added to approximately 100 μL retrieved blood. After 30 min incubation at 37° C., the cells were removed by 10 min centrifugation at 2,000 rpm, 50 μL PBS was added to 50 μL of the plasma, followed by addition of 45 μL of 15% TCA. The rest of the analysis was done as described for the serum stability studies. Control blood was treated identically without A3-APO peptide addition. As shown in the lower panel of FIG. 2, the unmodified A3-APO peptide with an M/z of 5033 was still present, but in significantly lower quantities. While the double charged ion at 2519 M/z from the serum studies could not be detected, the two serum components at 1798 and 2969 M/z and two new peaks at 2321 and 2577 M/z were present. These latter peptide species correspond to stable early degradation products.

Table 1 summarizes the A3-APO fragments detected in the blood preparations. Z is 1-cyclohexane-carboxylic acid (Chex) and X is 2,4-diamino butyric acid (Dab). The A3-APO degradation fragment at 2321 M/z corresponds to the peptide Chex1-Val19 (SEQ ID NO:4) The molecular weight (MW) of the Chex1-Val19 fragment is 2318 Da. The A3-APO degradation fragment at 2577 M/z corresponds to the peptide Chex1-Dab21. The molecular weight of the Chex1-Dab21 fragment is exactly 2577 Da.

TABLE 1

| Peptide | Calculated mass (Da) | Present in | M/z |
|---|---|---|---|
| (SEQ ID NO: 2)$_2$-Dab | 5034 | Serum in vitro | 5035 |
| Chex-Arg-Pro-Asp-Lys-Pro-Arg-Pro-Tyr-Leu-Pro-Arg-Pro-Arg-Pro-Pro-Arg-Pro-Val (SEQ ID NO: 4) | 2318 | Blood ex vivo | 2321 |
| Chex-Arg-Pro-Asp-Lys-Pro-Arg-Pro-Tyr-Leu-Pro-Arg-Pro-Arg-Pro-Pro-Arg-Pro-Val-Arg-Dab (SEQ ID NO: 7) | 2577 | Blood ex vivo | 2577 |

Although the peak heights in mass spectroscopy are not linearly dependent upon the load of the analytes, the lower panel of FIG. 2 indicates that the quantities of degradation products well exceed those of the intact peptide. Based on this analysis, the degradation rate of peptide A3-APO appeared to significantly increase going from in vitro serum to ex vivo blood preparations. A potential reason for this may be that the peptide is cleaved by proteases residing in different cells of blood, such as thimet oligopeptidase, which preferentially cleaves peptides between valine, leucine or other hydrophobic amino acids and positively charged residues (Dando et al., 1993. *Biochem. J.* 294: 451-457). This would result in the sequence features of the ex vivo observed degradation products. These enzymes, of course, are not significantly present in the serum and plasma preparations used during the in vitro stability studies.

Example 1

Analysis of A3-APO Peptide Degradation Fragments from Blood of A3-APO Injected Mice: Identification of Chex1-Arg20 Peptide Peptide was injected into three mice intravenously. Specifically, one hundred μg peptide A3-APO (5 mg/kg) dissolved in 200 μL sterile PBS pH 7.2 was injected either intravenously to the tail vein (for pharmacokinetics study) or subcutaneously (dorsally, around the shoulder blade, for immunization studies) into healthy CD-1 mice (Charles River Laboratories) using three mice for each timepoint. For the pharmacokinetics studies, about 100 μL blood was taken from the eye at 0 (right after peptide administration), 5, 15, 30, 90, 120 and 240 minutes. Each animal was used only at two timepoints. Cells were centrifuged and 20 μL 15% TCA was added per 100 μL of plasma. After repeated centrifugation, 10 μL supernatant was loaded to both a Voyager DE matrix-assisted laser ionization/desorption time-of-flight (MALDI-TOF) mass spectrometer (Applied Biosystems, Foster City, Calif.) and a C18 narrowbore HPLC column (2.1 mm/20 cm) that had previously been calibrated with 10 ng, 30 ng and 100 ng peptide A3-APO dissolved in PBS. Absorbance was measured at 214 nm. RP-HPLC failed to identify unmodified A3-APO peptide in any of the samples, suggesting that the peptide completely decomposed in vivo, or was present only insomuch as it was below our detection level of approximately 0.5 μg in 50 μL blood (less than 10% of the injected amount). By MS without peptide present, two peaks could be identified at 2910 and 4965 M/z, while the double charged peaks of these species could not be detected.

Figure 3:
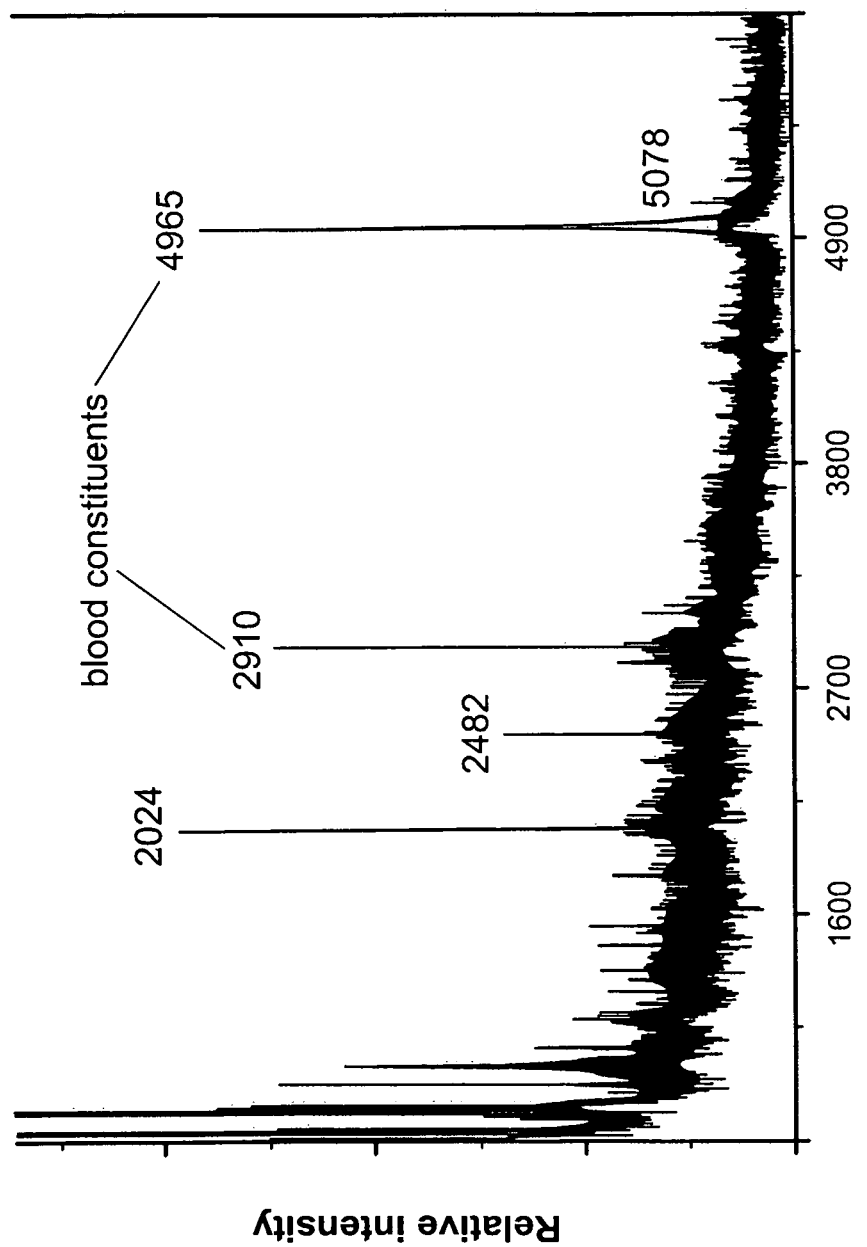
FIG. 3 illustrates A3-APO fragments detected in various blood preparations. A3-APO was injected into CD-1 mice intravenously, and after 30 minutes blood was taken, the cells and plasma proteins were removed, and the peptide was submitted to matrix-assisted laser desorption/ionization flight-of-time mass spectroscopy analysis. The spectrum shows a representative sample selected from 3 parallel groups.

Referring now to FIG. 3, the mass spectrum taken at 30 minutes after peptide administration is illustrated. The peak at 4965 M/z could also be seen during the ex vivo assay, albeit at lower quantities as compared with the lower panel of FIG. 2. The 2910 M/z blood component was new for the PK assay and the 2969 M/z peak detected in serum and blood was no longer visible. The 1798 M/z blood component appeared at a later timepoint of 90 minutes (not shown). At 30 minutes, the MS peak representing the unmodified peptide A3-APO was absent from the spectrum, unless the minor peak at 5078 M/z corresponded to the potassium adduct (calculated MW: 5074 Da). Indeed, the A3-APO peptide appeared to have almost completely decomposed in vivo. Also shown in FIG. 3, two new major peptide-derived peaks could be observed at 2482 and 2024. Table 2 summarizes the A3-APO fragments detected in the blood preparations as represented by the new peaks observed at 2482 and 2024. The peak at 2482 corresponded to the single chain Chex 1-Arg20 fragment.

TABLE 2

| Peptide | Calculated mass (Da) | Present in M/z | |
|---|---|---|---|
| (SEQ ID NO: 1)-Dab-Arg | 2014 | Blood in vivo | 2024 |
| Chex-Arg-Pro-Asp-Lys-Pro-Arg-Pro-Tyr-Leu-Pro-Arg- | 2475 | Blood in vivo | 2482 |

TABLE 2-continued

| Peptide | Calculated mass (Da) | Present in M/z |
|---|---|---|
| Pro-Arg-Pro-Pro-Arg-Pro-Val-Arg (SEQ ID NO: 2) | | |

The peptides in Table 2 were already present 5 minutes after peptide inoculation, and their quantities increased by 30 minutes. By 90 minutes, the quantity of the 2024 M/z peak further increased and that of the 2482 M/z decreased relative to the two blood-derived components. None of the new A3-APO-derived peaks were observable at 120 or 240 minutes. Only the blood components at 1798 (dominant) and 2910 (minor) were visible.

The calculated MW of the single chain Chex1-Arg20 fragment was 2474 Da that corresponded to the 2482 M/z peak, within the experimental error of mass spectrometry in biological media. The 2024 M/z product likely corresponded to the Arg7-Arg(−1) fragment. In addition to the cleavage site around the C-terminal arginines, major cleavage sites for both pyrrhocoricin and drosocin are located approximately 5-7 residues from the amino termini (Hoffmann et al., 1999. *Biochim. Biophys. Acta* 1426: 459-467). In spite of the sequence optimization process that resulted in improved cell penetrating and antimicrobial activity (Otvos et al., 2005. *J. Med. Chem.* 48: 5349-5359), the conserved architecture of the proline-rich antimicrobial peptides apparently retained the major proteolytic degradation sites.

Experimental Example 2

Activity of Synthesized Chex1-Arg20 Peptide

To investigate the activity of the A3-APO metabolites, Chex1-Arg20 single chain unit and an Arg7-Arg20 common cleavage fragment were synthesized and studied for their ability to kill Enterobacteriaceae strains in undiluted Muller-Hinton broth, a true measure of potential clinical viability (Otvos et al., 2005. *J. Med. Chem.* 48: 5349-5359). The peptides of the invention were made on a CEM Liberty automated synthesizer with standard Fmoc-chemistry. The peptides were detached from the resin with the carboxyl terminus of the C-terminal Arg residue being in the form of an amino amide, —C(O)—NH$_2$ ("Chex1-Arg20-NH$_2$" and "Arg7-Arg20-NH$_2$"), while still in the microwave chamber, and were purified by RP-HPLC. MALDI-MS verified the accuracy of the sequences and their high purity. The amino acid sequence of Arg7-Arg20 is: Arg-Pro-Tyr-Leu-Pro-Arg-Pro-Arg-Pro-Pro-Arg-Pro-Val-Arg (SEQ ID NO:1). The biological studies carried out on chemically synthesized peptides in this example and succeeding examples were carried out on the C-terminal modified versions of the peptides wherein the C-terminal carboxylic acid function was in the form of an amide, —C(O)—NH$_2$. Antibacterial growth inhibition assays were performed using sterile 96-well polypropylene plates (Nunc F96 microtiter plates) in a final volume of 100 μL as described previously (Cudic et al., 2002. *Peptides* 23: 271-283). The cell concentrations were estimated by measuring the ultraviolet absorbance at 600 nm and applying the formula cfu/mL=A$_{600}$(3.8×10$^8$), where cfu is the number of colony-forming units. Briefly, 50 μL of a suspension of midlogarithmic phase bacterial cultures diluted to 5×10$^5$ cfu/mL in Muller-Hinton broth (MHB) was added to 50 μL of serially diluted peptides also dissolved in MHB. The final peptide concentration was 128 μg/mL. Cultures were then incubated at 37° C., 5% CO$_2$ for 16-20 h without shaking, and growth inhibition was measured by recording the absorbance at 600 nm using a microplate reader. MBCs were identified as the lowest antimicrobial doses when the 600 nm absorbance did not exceed that of the negative control medium only values. Table 2 identifies the activity of antimicrobial peptides against multidrug resistant clinical isolates. The minimal inhibitory concentration indicates the lowest peptide dose where no visible bacterial growth is detected after 16 hours incubation in full strength Muller-Hinton broth at 37° C. The peptide Chex-pyrr-Dap dimer was also included in the study. The peptide Chex-pyrr-Dap dimer includes the sequence: Asp-Lys-Gly-Ser-Tyr-Leu-Pro-Arg-Pro-Thr-Pro-Pro-Arg-Pro-Ile-Tyr-Asn-Arg (SEQ ID NO:5), where the peptide dimer has a sequence of Chex-(SEQ ID NO:5)$_2$O, where 0 is a monoacetyled dimer of 1,3-diamino propionic acid [Dap-Dap(Ac)] (Cudic et al., 2002. *Peptides* 23: 271-283).

The results are shown in Table 3. The shorter Arg7-Arg20 fragment exhibited MIC values >64 µg/mL against the test strain. The negative control Chex-pyrr-Dap dimer remained without significant activity in full-strength Muller-Hinton broth as expected (Cudic et al., 2003. *Peptides* 24: 807-820).

TABLE 3

| Peptide | MIC (µg/mL) against | | | | |
| --- | --- | --- | --- | --- | --- |
| | E. coli HK179 | E. coli D31 | E. coli SEQ102 | K. pneumoniae HK123 | S. typhimurium G10215 |
| A3-APO | 8 | 2 | 16 | 16 | 16 |
| Metabolite 2482 M/z (Chex1-Arg20) | 2 | 8 | 32 | 8 | 4 |
| Arg7-Arg20 common in vivo cleavage product | >64 | >64 | >64 | >64 | >64 |
| Chex-pyrr-Dap dimmer | >64 | >64 | >64 | >64 | >64 |

As shown in Table 3, Chex1-Arg20 was overall twice as potent as A3-APO in killing resistant bacteria. The measured minimal bactericidal concentrations (MBC) values were 2-32 µg/mL, 8 µg/mL and 4 µg/mL against *Escherichia coli*, *Klebsiella pneumoniae*, and *Salmonella typhimurium* isolates with $IC_{50}$ values between 100 nM and 500 nM.

Example 3

Antibacterial Activity Comparison of A3-APO and Chex1-Arg20 Peptides

Following the protocol of Example 2, minimal inhibitory concentrations of the Chex1-Arg20 peptide against selected bacteria was determined. MIC was determined in an overnight liquid growth inhibition assay in quarter strength Mueller-Hinton broth at 37° C. A3-APO was included for comparison. The results are set forth in Table 4.

TABLE 4

| Bacterial Strain | A3-APO MIC (µg/mL) | Chex1-Arg20 MIC (µg/mL) |
| --- | --- | --- |
| E. coli HK101 | 2 | 0.5 |
| E. coli HK179 | 2 | 1 |
| E. coli SOTE40 | 8 | 2 |
| E. coli 5770 | 2 | 0.5 |
| E. coli HK131 | 4 | 1 |
| E. coli SEQ102 | 2 | 1 |
| E. coli 045-849 | 4 | 2 |
| K. pneumoniae HK 123 | 4 | 2 |
| K. pneumoniae HK 186 | 8 | 0.25 |
| K. pneumoniae HK 127 | 8 | 0.25 |
| K. pneumoniae 012-3132 | 2 | 0.25 |
| K. pneumoniae K6 | 4 | 2 |

TABLE 4-continued

| Bacterial Strain | A3-APO MIC (µg/mL) | Chex1-Arg20 MIC (µg/mL) |
| --- | --- | --- |
| S. typhimurium ATCC 14028 | 8 | 1 |
| S. typhimurium S5 | 8 | 0.5 |
| S. typhimurium G10215 | 4 | 0.25 |
| P. aeruginosa ATCC 39329 | 8 | 32 |
| P. aeruginosa 10 | 8 | 32 |
| S. saprophyticus ATCC 15305 | 2 | 4 |
| A. baumannii ATCC BBA-1605 | 16 | 16 |

Ex vivo blood stability studies were repeated on Chex1-Arg20 according to the protocol described above "Stability of Peptide A3-APO in Whole Blood". Chex1-Arg20 was almost completely stable within the entire 120 min examination period. The only degradation product that could be detected, at about one third of the peak height of the Chex1-Arg20 starting material, was at 2321 M/z, representing a fragment with the C-terminal arginine missing. Apparently this cleavage product is the Chex1-Val19 fragment observed for peptide A3-APO when the stability studies were done in blood ex vivo (see and compare with the lower panel of FIG. 2 and Table 1). Taken together, the Chex1-Arg20 single chain fragment of A3-APO represents the major A3-APO degradation product in blood preparations and is stable in the biological environment where peptide A3-APO has to otherwise exert its activity against infections caused by resistant enteric bacteria.

Example 4

In Vivo Efficacy of Synthesized Chex1-Arg20 Peptide

To further illustrate that the Chex1-Arg20 fragment corresponds to the active in vivo metabolite of the prodrug A3-APO, and that it is suitable for the eradication of resistant Enterobacteriaceae, in vivo efficacy studies were carried out on an animal model of systemic infections.

As peptide drugs, such as antimicrobial peptides, are predominantly cleared through the kidneys (Klootwijk et al., 1997. *J. Clin. Endocrinol*. Metab. 82: 3068-3073) and the kidney functions of mice are 20-fold faster than those of humans, CD-1 female mice of 15-20 g were pretreated with 18 mg/kg cisplatin for 3 days to impair kidney clearance similar to the levels observed in humans (Mathe et al., 2006. *Lab. Anim*. 40: 296-300) before they were challenged intraperitoneally (ip) with $10^8$ CFU per g mouse of an extended-spectrum β-lactamase producing *E. coli* strain (designation 5770). Four, 8 and 12 hours after challenge 10 or 20 mg/kg peptide Chex1-Arg20 or 40 mg/kg imipenem (as a positive control) were administered ip to 10 mice in each group. Imipenem is a broad spectrum β-lactam antibiotic. Prior to drug administration at all three timepoints, blood was taken from the tail vein of 3-5 mice for determining blood bacterial counts. Table 5 shows the effect of peptide Chex1-Arg20 on blood bacterial counts of mice pretreated with 18 mg/kg cisplatin for 3 days and challenged intraperitoneally with $1 \times 10^8$ cfu/g of extended spectrum β-lactamase-producing *E. coli* 5770 strain. Antimicrobials were administered ip 4 hours after challenge 3 times in 4 hour intervals. Blood was taken immediately before antimicrobial treatments. Numbers in parentheses indicate the number of mice with $<10^3$ CFU/mL. Bacterial counts were determined 10 times from different dilution of blood from 5 mice in each group in each timepoints.

TABLE 5

| Treatment | Bacterial counts in blood (CFU/mL) after Inoculation/challenge | | |
|---|---|---|---|
| | 4 h | 8 h | 12 h |
| No treatment (bacterium only) | $3.2 \times 10^5$ | $2.4 \times 10^6$ | $9.7 \times 10^6$ |
| Chex1-Arg20 peptide at 10 mg/kg | $3.2 \times 10^5$ | $8.2 \times 10^3$ (1/5) | $<1.3 \times 10^4$ (1/5) |
| Chex1-Arg20 peptide at 20 mg/kg | $3.2 \times 10^5$ | $5.5 \times 10^4$ (3/5) | $<3.7 \times 10^3$ (3/5) |
| Imipenem at 40 mg/kg | $3.2 \times 10^5$ | $3.7 \times 10^3$ (3/5) | $<1.2 \times 10^3$ (3/5) |

As shown in Table 5, blood bacterial counts amounted to $10^5$ CFU/mL by 4 hours after challenge and exceeded $10^7$ CFU/mL after 12 hours in untreated mice. The Chex1-Arg20 peptide reduced the bacterial counts in a dose- and time-dependent manner. While at 10 mg/kg, the bacterial counts were reduced by approximately 3 log 10 units with only one mouse showing no bacteria at all, after two doses of 20 mg/kg peptide, a 3.5 log 10 units bacterial count reduction was observed with 60% of the mice having blood bacterial levels below our detection limits. This efficacy level is similar to that produced by an identical imipenem treatment at 40 mg/kg doses. It should be noted that due to the arbitrary more than zero bacterial counts assigned to mice with bacteria below the 1000 cfu/mL detection limit and to single outlier mice with high cfu counts, the bacterial loads were only approximate and in reality were lower than the numerical values given in Table 5 (as indicated by the < sign).

A gross necropsy of the surviving mice three days post-infection showed no signs of toxicity at either Chex1-Arg20 peptide dose. The skin was smooth, and healthy liver, lungs, spleen and kidneys were registered. There were no signs of internal bleeding (hemolysis), which may be a side reaction of antimicrobial peptides in systemic use. The pharmacokinetic parameters together with the in vivo efficacy data show that the Chex1-Arg20 metabolite is suitable for use against systemic infections caused by sensitive strains.

Example 5

Comparison of In Vivo Efficacy of Synthesized Chex1-Arg20 Peptide and A3-APO

Figure 4A:
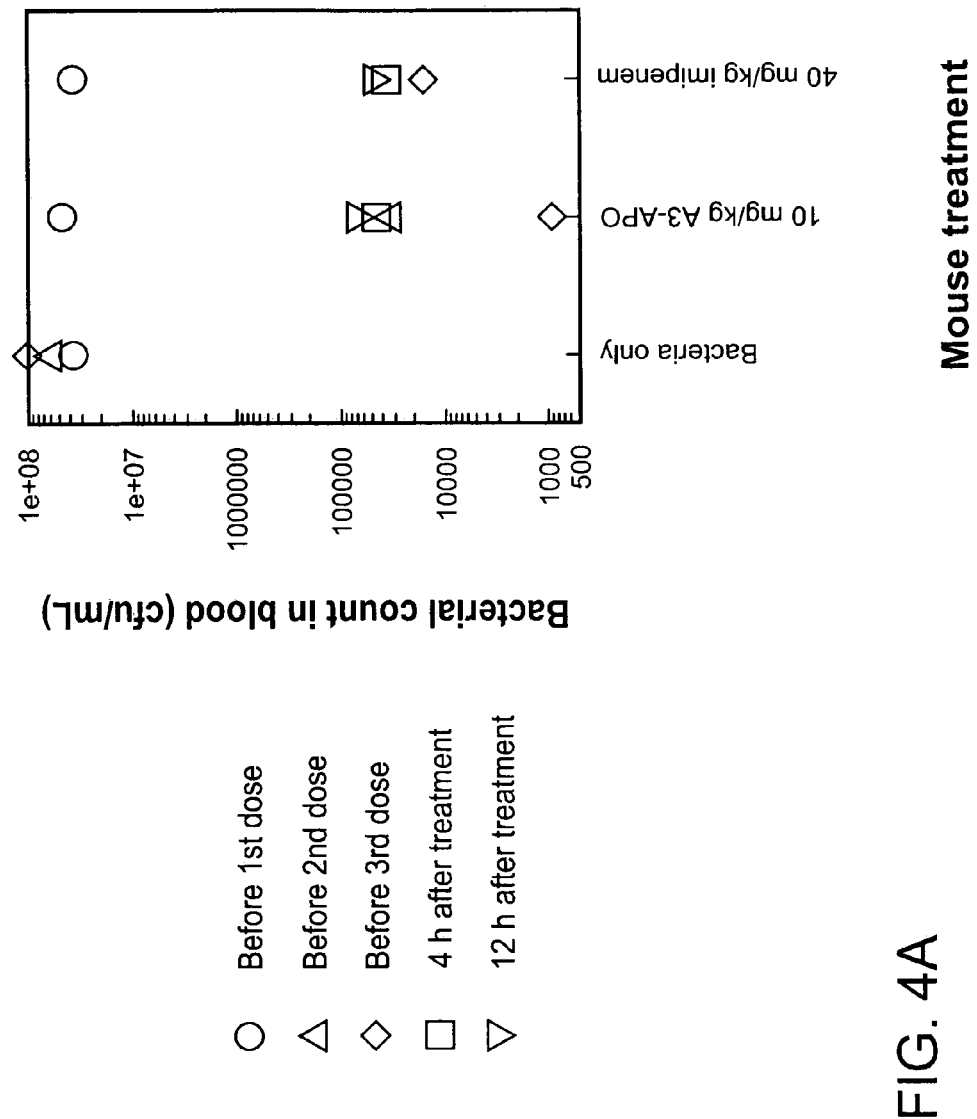
FIGS. 4A and 4B illustrate blood bacterial counts before and after intraperitoneal drug dosing to *Escherichia coli* 5770 infected CD-1 mice.
Figure 4B:
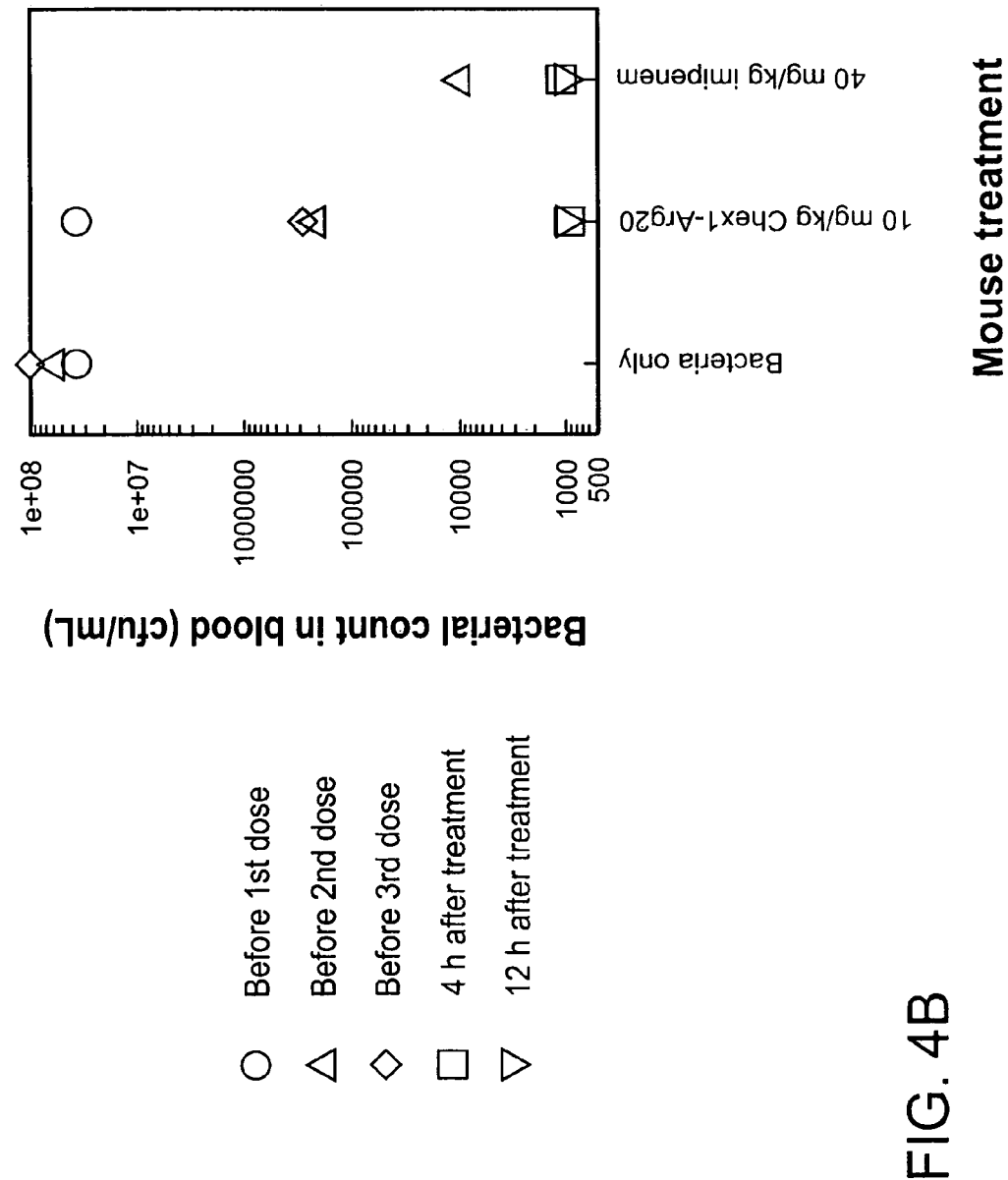

Both A3-APO and Chex1-Arg20 are active in lethal systemic infections. Efficacy is shown in both the increase of survival time and the reduction of blood bacterial counts. FIGS. 4A and 4B show blood bacterial counts before and after intraperitoneal drug dosing to *Escherichia coli* 5770 infected CD-1 mice. In FIG. 4A the symbols represent bacterial counts observed for infected and non-treated mice, A3-APO treated mice and imipenem treated mice. In FIG. 4B the symbols represent bacterial counts observed for infected and non-treated mice, Chex1-Arg20-NH$_2$ treated mice and imipenem treated mice. Identical shapes if FIGS. 4A and 4B represent identical timepoints, respectively. Treatment with peptide A3-APO or with the Chex1-Arg20-NH$_2$ reduced the bacterial counts to levels identical to those observed after imipenem treatment in the respective assays.

Example 6

Comparison of Mouse Survival Rate After Treatment

The survival rate and the dynamics of survival of mice after the last dose of an antibacterial peptide treatment (12 hours post-infection) were measured in a mouse model of *Escherichia coli* 5770 systemic infection. In this particular study, the animals were not pretreated with cisplatin. Ten animals were used in each group. As shown in Table 6, bold numbers indicate the number of surviving mice treated with the Chex-1-Arg20 peptide, and underlined numbers are those surviving mice that received A3-APO as a treatment option. In the control (infected, non-treated) and the imipenem treated rows, the first numbers reflect the number of surviving animals on the day of assay measuring the efficacy of the Chex1-Arg20 and the second numbers are the surviving control animals on the day of the A3-APO efficacy assay.

TABLE 6

| Treatment groups (10 animals each) | 0 h | 3 h | 6 h | 9 h | 12 h |
|---|---|---|---|---|---|
| Infected, non-treated | 10/9 | 5/6 | 2/2 | 1/1 | 1/1 |
| 2.5 mg/kg Chex1-Arg20/A3-APO | 10/9 | 7/7 | 7/2 | 5/1 | 4/1 |
| 5 mg/kg Chex1-Arg20/A3-APO | 9/10 | 9/6 | 8/5 | 6/3 | 5/3 |
| 10 mg/kg Chex1-Arg20/A3-APO | 10/9 | 10/9 | 10/8 | 9/3 | 5/2 |
| 40 mg/kg imipenem | 10/9 | 10/9 | 10/9 | 10/9 | 10/9 |

The above data demonstrates that Chex1-Arg20 peptide actually exhibits increased antimicrobial properties in vivo than A3-APO itself. Indeed, at 20 mg/kg the Chex1-Arg20 metabolite sterilized mouse blood after a lethal *E. coli* infection. Chex1-Arg20 is, on average, twice as active in milligram/L terms, and 5 times in molar terms. As Chex1-Arg20 is less than half the size of A3-APO, Chex1-Arg20 is much easier to mass produce. With this in mind, Chex1-Arg20 will be preferred for treatment of bacterial infections over A3-APO.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. An isolated and purified compound of the formula (SEQ ID NO: 6)
X$_1$-X$_2$-Pro-X$_3$-X$_4$-Pro-Arg-Pro-Tyr-Leu-Pro-X$_5$-Pro-Arg-Pro-Pro-Arg-Pro-Y wherein;
(a) X$_1$ is selected from the group consisting of:
 (i) a natural or non-natural amino acid having a free amino group, and
 (ii) 1-amino-cyclohexyl carboxylic acid,
(b) X$_2$ is Arg or N-methyl-Arg,
(c) X$_3$ is Asp or Glu,
(d) X$_4$ is Arg or Lys,
(e) X$_5$ is Arg or Lys, and
(f) Y is Arg, Arg-NH$_2$, N-methyl-Arg, N-methyl-Arg-NH$_2$, Val-Arg, Val-Arg-NH$_2$, Val-(N-methyl-Arg), or Val-(N-methyl)-Arg-NH$_2$, or a salt thereof.

2. A compound according to claim 1, wherein the compound is Chex-Arg-Pro-Asp-Lys-Pro-Arg-Pro-Tyr-Leu-Pro-Arg-Pro-Arg-Pro-Pro-Arg-Pro-Val-Arg (SEQ ID NO:2) or Chex-Arg-Pro-Asp-Lys-Pro-Arg-Pro-Tyr-Leu-Pro-Arg-Pro-Arg-Pro-Pro-Arg-Pro-Val-Arg-NH$_2$ (SEQ ID NO:3), or a salt thereof.

3. A pharmaceutical composition comprising at least one compound of claim 1, or a salt thereof, and a pharmaceutically acceptable carrier.

4. A pharmaceutical composition according to claim 3, wherein the compound is Chex-Arg-Pro-Asp-Lys-Pro-Arg-Pro-Tyr-Leu-Pro-Arg-Pro-Arg-Pro-Pro-Arg-Pro-Val-Arg (SEQ ID NO:2) or Chex-Arg-Pro-Asp-Lys-Pro-Arg-Pro-Tyr-Leu-Pro-Arg-Pro-Arg-Pro-Pro-Arg-Pro-Val-Arg-NH$_2$ (SEQ ID NO:3), or a salt thereof.

5. The pharmaceutical composition of claim 3, further comprising a non-peptide antibiotic.

6. A method of treating a bacterial infection in a subject in need of such treatment, the method comprising administering to the subject an effective amount of an isolated and purified compound of claim 1, or a salt thereof.

7. The method of claim 6, wherein the compound is Chex-Arg-Pro-Asp-Lys-Pro-Arg-Pro-Tyr-Leu-Pro-Arg-Pro-Arg-Pro-Pro-Arg-Pro-Val-Arg (SEQ ID NO:2) or Chex-Arg-Pro-Asp-Lys-Pro-Arg-Pro-Tyr-Leu-Pro-Arg-Pro-Arg-Pro-Pro-Arg-Pro-Val-Arg-NH$_2$ (SEQ ID NO:3), or a salt thereof.

8. The method of claim 6 or 7, wherein the organism causing the bacterial infection is, *Staphylococcus saprophyticus*.

9. The method of claim 6 or 7, wherein the organism causing the bacterial infection is *Acinetobacter baumannii* or *Pseudomonas aeruginosa*.

10. The method of claim 6 or 7, wherein the organism causing the bacterial infection is a member of the family Enterobacteriaceae.

11. The method of claim 10, wherein the organism is *Escherichia coli*, *Klebsiella pneumoniae*, or *Salmonella typhimurium*.

12. The method of claim 10, wherein the organism is *Enterobacter cloacae*.

13. The method of claim 10, wherein the organism is *Haemophilus influenzae*.

* * * * *